United States Patent
Okuda

(10) Patent No.: US 12,042,406 B2
(45) Date of Patent: Jul. 23, 2024

(54) MULTI-ARTICULATED LINK KNEE JOINT

(71) Applicant: NABTESCO CORPORATION, Tokyo (JP)

(72) Inventor: Masahiko Okuda, Hyogo (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 17/682,775

(22) Filed: Feb. 28, 2022

(65) Prior Publication Data

US 2022/0175557 A1 Jun. 9, 2022

Related U.S. Application Data

(62) Division of application No. 16/380,227, filed on Apr. 10, 2019, now abandoned.

(30) Foreign Application Priority Data

Apr. 11, 2018 (JP) .................. 2018-076109

(51) Int. Cl.
*A61F 2/64* (2006.01)
*G01D 5/14* (2006.01)
*A61F 2/76* (2006.01)

(52) U.S. Cl.
CPC ............. *A61F 2/644* (2013.01); *G01D 5/142* (2013.01); *A61F 2002/7625* (2013.01); *A61F 2002/764* (2013.01)

(58) Field of Classification Search
CPC ............. A61F 2/642; A61F 2002/7625; A61F 2002/764; G01D 5/142
See application file for complete search history.

(56) References Cited

U.S. PATENT DOCUMENTS

| 5,383,939 | A | 1/1995 | James |
| 6,113,642 | A | 9/2000 | Petrofsky et al. |
| 7,066,964 | B2 | 6/2006 | Wild |
| 8,814,948 | B2 | 8/2014 | Pusch et al. |
| 9,351,855 | B2 | 5/2016 | Swift et al. |
| 9,532,877 | B2 | 1/2017 | Holgate |

(Continued)

FOREIGN PATENT DOCUMENTS

| JP | 2005034508 A | 2/2005 |
| JP | 2005111141 A | 4/2005 |

(Continued)

OTHER PUBLICATIONS

JPO Notification of Reasons for Refusal corresponding to JP Application No. 2018-076108; dated Jul. 5, 2022.

(Continued)

*Primary Examiner* — Bruce E Snow
(74) *Attorney, Agent, or Firm* — CANTOR COLBURN LLP

(57) ABSTRACT

A multi-articulated link knee joint includes: a knee unit in which an upper link unit rotates relative to a lower link unit by a multi-articulated link mechanism including a plurality of link units including the upper link unit and the lower link (Continued)

unit; a relative position detector for detecting a relative position of the upper link unit relative to the lower link unit; and an angle detector for obtaining a bending angle of the knee unit from the detected relative position.

1 Claim, 20 Drawing Sheets

(56) References Cited

U.S. PATENT DOCUMENTS

| | | | |
|---|---|---|---|
| 9,987,152 | B2 | 6/2018 | Chabloz et al. |
| 10,039,652 | B2 | 8/2018 | Zahedi et al. |
| 10,624,766 | B2 | 4/2020 | Battlogg |
| 2004/0193286 | A1 | 9/2004 | Grundei |
| 2008/0039756 | A1 | 2/2008 | Thorsteinsson et al. |
| 2014/0074243 | A1 | 3/2014 | Holgate |
| 2015/0032228 | A1* | 1/2015 | Shirata .................... A61F 2/644 623/39 |
| 2018/0028390 | A1* | 2/2018 | Dietl ........................ A61F 2/50 |
| 2018/0085234 | A1 | 3/2018 | Seifert et al. |
| 2019/0314172 | A1 | 10/2019 | Okuida |
| 2019/0314173 | A1 | 10/2019 | Okuida |
| 2021/0205101 | A1 | 7/2021 | Okuida |
| 2021/0282942 | A1 | 9/2021 | Okuida |
| 2022/0175557 | A1 | 6/2022 | Okuda |

FOREIGN PATENT DOCUMENTS

| | | |
|---|---|---|
| JP | 2007000616 A | 1/2007 |
| JP | 2009207789 A | 9/2009 |
| JP | 2013075342 A | 4/2013 |
| WO | 2013132662 A1 | 9/2013 |

OTHER PUBLICATIONS

JPO Notification of Reasons for Refusal corresponding to JP Application No. 2018-076109; dated Jul. 5, 2022.
JPO Notification of Reasons for Refusal for corresponding JP Application No. 2018-076108; dated Nov. 2, 2021.
JPO Notification of Reasons for Refusal for corresponding JP Application No. 2018-076109; dated Nov. 2, 2021.
USPTO Non-Final Office Action in U.S. Appl. No. 16/381,420, dated Sep. 22, 2020.
USPTO Non-Final Office Action for corresponding U.S. Appl. No. 17/336,842, Dated Apr. 3, 2023.

* cited by examiner

FIG.17

| SECOND SENSOR SECTION \ FIRST SENSOR SECTION | 0 | 1 |
|---|---|---|
| 0 | $\theta < B1$ | $B1 < \theta < B2$ |
| 1 | — | $B2 < \theta$ |

MULTI-ARTICULATED LINK KNEE JOINT

CROSS REFERENCE TO RELATED APPLICATION

The present application is a divisional application of U.S. patent application Ser. No. 16/380,227, filed on Apr. 10, 2019, the entire contents of which are incorporated herein by reference. The Ser. No. 16/380,227 application claimed the benefit of the date of the earlier filed Japanese Application No. 2018-076109, filed Apr. 11, 2018, priority to which is also claimed herein, and the contents of which are also incorporated by reference herein.

BACKGROUND OF THE INVENTION

1. Field of the Invention

The present invention relates to a multi-articulated link knee joint.

2. Description of the Related Art

Prosthetic legs used by people who had have their thigh cut above their knee due to a disease or an accident are coupled with an artificial knee joint that bends like a knee joint of a living body. When the artificial knee joint is bent depending on the motion of the user, motions such as standing, sitting, and walking are made possible.

Patent document 1 discloses an artificial knee joint including a knee unit that bends by a multi-articulated link mechanism and an air cylinder that assists the motion of the knee unit depending on the bending angle. In this artificial knee joint, since the multi-articulated link mechanism allows the motion of the knee unit to be similar to that of the knee joint of a living body, more natural motion is made possible. In addition, since walking motion is supported by a fluid cylinder, the stability of walking is improved.

[Patent document 1] WO2013/132662

The knee joint according to Patent document 1 detects the position of a piston rod connected to the knee unit, and a bending angle of the knee unit is obtained from the detection result to control an air cylinder. Other than air cylinders or hydraulic cylinders, there are cases where rotary hydraulic dampers having no piston rod are used as auxiliary drivers for assisting the motion of the knee unit. In this case, there is a need to change the configuration related to detection of the bending angle. If the configuration related to detection of the bending angle can be adapted to be compatible with auxiliary drivers of different types, there is a possibility that cost can be reduced by sharing parts in deploying various product groups.

SUMMARY OF THE INVENTION

The present invention has been made in view of these challenges, and it is an object of the present invention to adapt a configuration for detecting a bending angle of a knee unit in a multi-articulated link knee joint to be compatible with auxiliary drivers of a plurality of types.

One embodiment of the present invention is a multi-articulated link knee joint. This multi-articulated link knee joint includes: a knee unit in which an upper link unit is rotates relative to a lower link unit by a multi-articulated link mechanism including a plurality of link units including the upper link unit and the lower link unit; a relative position detector for detecting a relative position, relative to a certain link unit among the plurality of link units, of another link unit; and an angle detector for obtaining a bending angle of the knee unit from the detected relative position.

According to this embodiment, the relative position of the other link unit relative to the certain link unit among the plurality of link units is detected, and the bending angle of the knee unit is obtained from the detection result, and thus auxiliary drivers of different types can be covered by similar configurations.

BRIEF DESCRIPTION OF THE DRAWINGS

FIG. 17 is a table illustrating combinations of sections of the first angle sensor and sections of the second angle sensor;

DETAILED DESCRIPTION OF THE INVENTION

Figure 1:
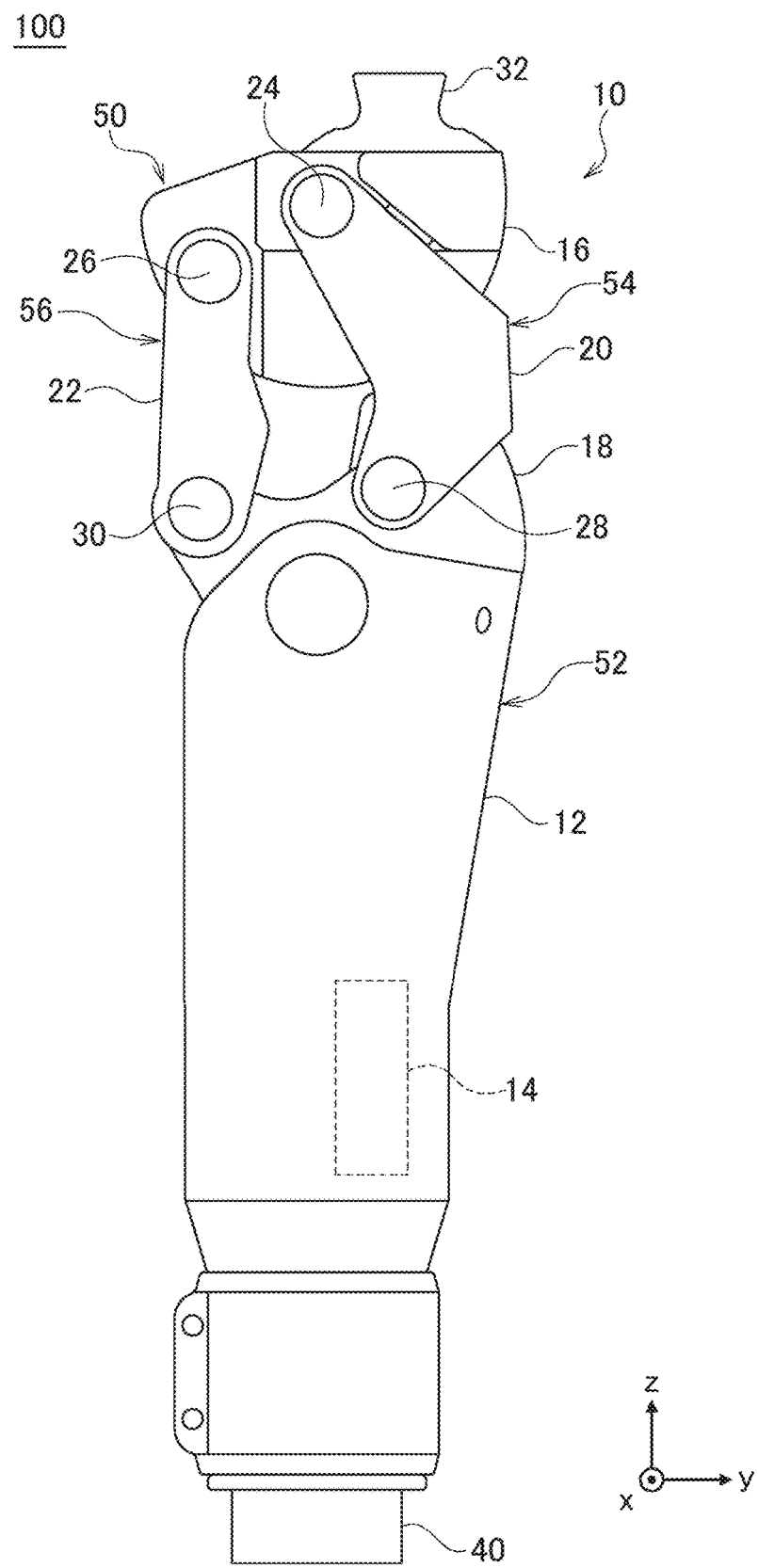
FIG. 1 is a side view of a multi-articulated link knee joint according to a first embodiment of the present invention.

The invention will now be described by reference to the preferred embodiments. This does not intend to limit the scope of the present invention, but to exemplify the invention.

Hereinafter, in embodiments, the same component is denoted by the same symbol, and redundant explanations are omitted. In addition, for convenience of explanation, a part of a component is omitted as appropriate in the drawings.

Before specifically explaining a multi-articulated link knee joint according to an embodiment, the overview will be explained. A multi-articulated link knee joint according to an embodiment includes a knee unit in which an upper link unit rotates relative to a lower link unit by a multi-articulated link mechanism and an auxiliary driver for assisting the motion of the knee unit. An example of the auxiliary driver is a rotary hydraulic damper. The multi-articulated link knee joint includes a relative position detector that detects a relative position, relative to a certain link unit among a plurality of link units, of another link unit. This relative position may be, for example, a distance from the certain link unit to the other link unit, a rotation angle of the other link unit to the certain link unit, and so on. The bending angle of the knee unit can be obtained from the detected relative position. The auxiliary driver may be a cylinder device such as an air cylinder or a hydraulic cylinder. According to a knee joint according to the present embodiment, auxiliary drivers of different types can be covered by similar configurations to detect the bending angle of a knee unit.

First Embodiment

Figure 2:
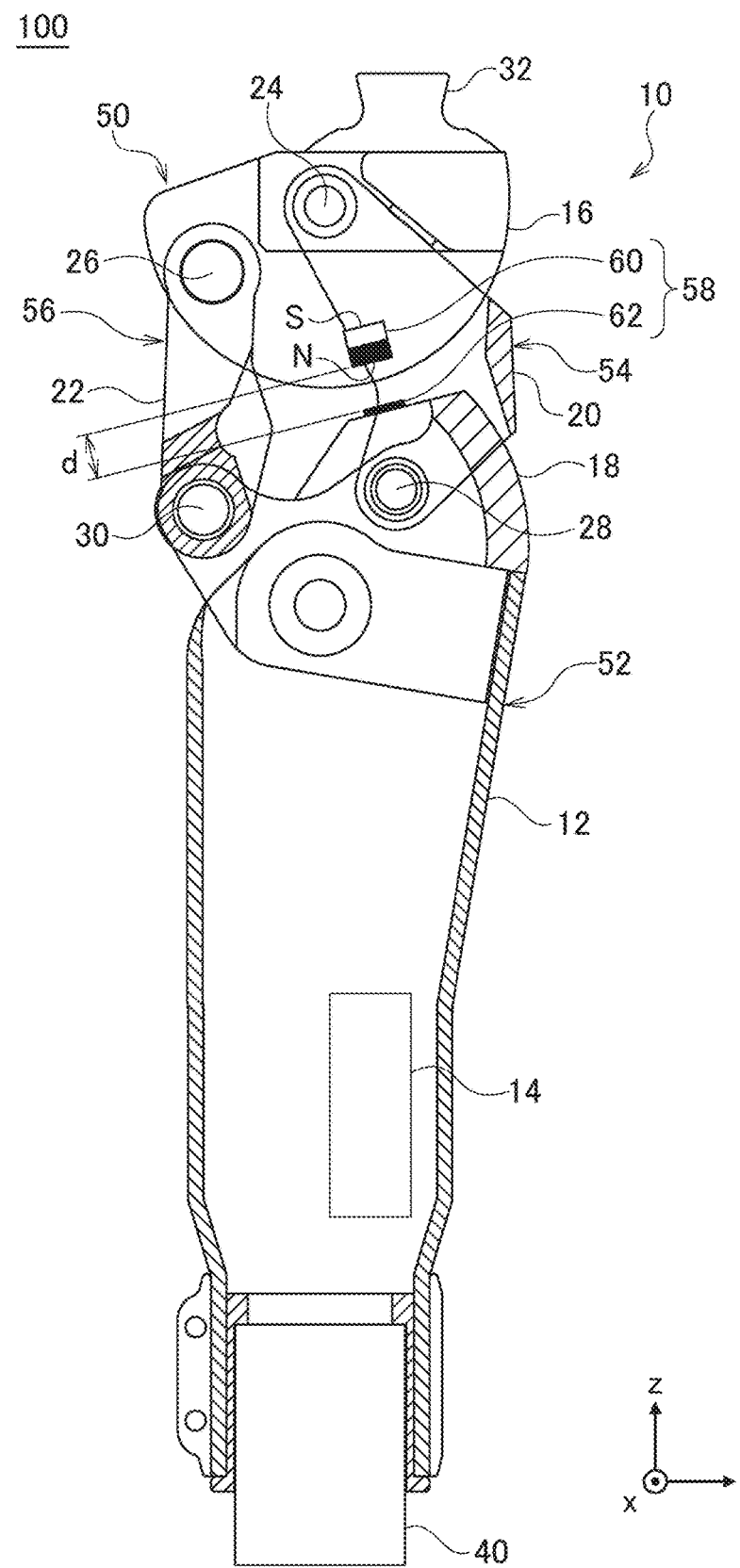
FIG. 2 is a schematic cross-sectional view of the multi-articulated link knee joint according to the first embodiment of the present invention.

FIG. 1 is a side view of a multi-articulated link knee joint 100 according to a first embodiment of the present invention. FIG. 2 is a schematic cross-sectional view of the multi-articulated link knee joint 100 according to the first embodiment of the present invention. In the following description, in an xyz orthogonal coordinate system illustrated in each drawing, a direction parallel to the x axis is defined as the lateral direction, and the positive direction of the x axis is referred to as "left" with the negative direction referred to as "right." A direction parallel to the y axis is defined as the anterior-posterior direction, and the positive direction of they axis is referred to as "anterior" with the negative direction referred to as "posterior." A direction parallel to the z axis is defined as the vertical direction, and the positive direction of the z axis is referred to as "up" with the negative direction referred to as "down."

The multi-articulated link knee joint 100 includes a knee unit 10. The knee unit 10 is bent by a multi-articulated link mechanism having a plurality of link units. In the first embodiment, the multi-articulated link mechanism is a four-articulated link mechanism including four link units of an upper link unit 50, a lower link unit 52, an anterior link unit 54, and a posterior link unit 56. In this specification, a link and parts secured to the link to move in conjunction with the link are collectively referred to as a "link unit." The upper link unit 50 includes an upper link 16 and a thigh connector 32. The lower link unit 52 includes a lower link 18 and an lower leg part 12. The anterior link unit 54 includes an anterior link 20. The posterior link unit 56 includes a posterior link 22.

The upper link 16 is provided with a first shaft 24 and a second shaft 26, and the lower link 18 is provided with a third shaft 28 and a fourth shaft 30. Each of the shafts is provided such that the axial direction thereof is parallel to the x axis and so as to be rotatable. The anterior link 20 is attached to the ends of the first shaft 24 and the third shaft 28. The posterior link 22 is attached to the ends of the second shaft 26 and the fourth shaft 30. The upper link 16 is supported by the anterior link 20 and the posterior link 22 and rotates relative to the lower link 18.

The lower leg part 12 is formed in a cylindrical shape and is secured under the lower link 18. Furthermore, provided under the lower leg part 12 is a leg connector 40 which is connected to a leg part included in a prosthetic leg.

The thigh connector 32 protruding from the upper link 16 is connected to a socket attached to the thigh of a user. An angle formed by the direction in which the thigh connector 32 protrudes and the z axis is defined as the bending angle of the knee unit 10. The bending angle illustrated in FIG. 1 and FIG. 2 is 0°, which is a state in which the knee unit 10 is completely extended.

Figure 3:
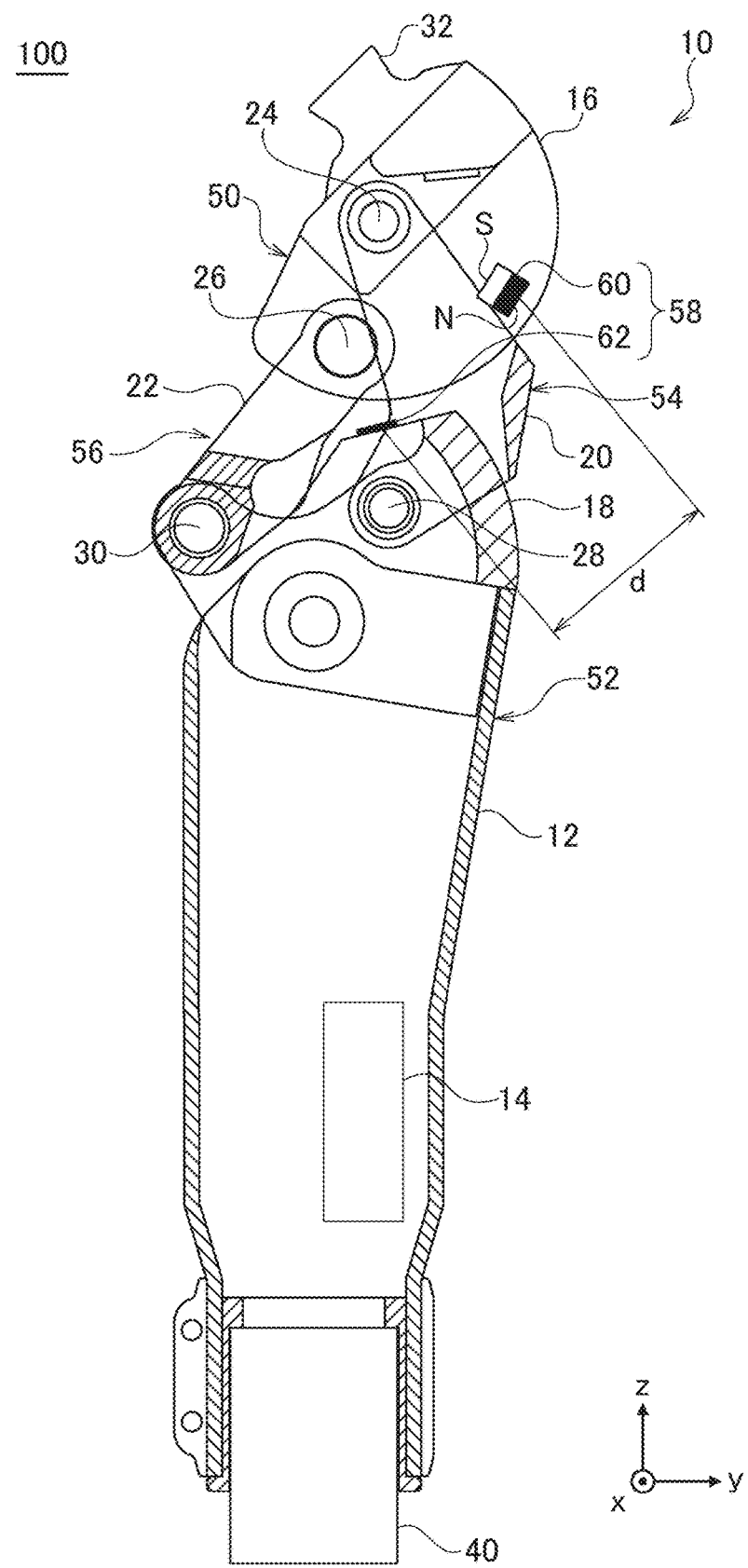
FIG. 3 is a view illustrating a state in which a knee unit is bent by 45° in the multi-articulated link knee joint according to the first embodiment.

FIG. 3 is a view illustrating a state in which the knee unit 10 is bent by 45° in the multi-articulated link knee joint 100 according to the first embodiment. When the bending angle is large, the anterior link 20 and the posterior link 22 intersect. The upper link 16 rotates while moving backward relative to the lower link 18. Due to the rotation of the upper link 16, the knee unit 10 bends like the knee joint of a living body does.

The multi-articulated link knee joint 100 further includes a relative position detector 58 for detecting the relative position of the upper link unit 50 relative to the lower link unit 52. The relative position detector 58 includes a magnet 60 and a magnetic sensor 62 for detecting the intensity of the magnetic field generated by the magnet 60. The magnet 60 may be, for example, a rectangular alnico magnet. The magnetic sensor 62 may be, for example, a Hall element. The magnetic sensor 62 is provided at a predetermined portion of the lower link 18, for example, on the lower link 18. The magnet 60 is provided at a predetermined portion of the upper link 16, for example, at a portion that approaches close to the magnetic sensor 62 when the bending angle is 0°. The magnet 60 is arranged such that the N pole faces the magnetic sensor 62 and the S pole faces the opposite side to the magnetic sensor 62 when the bending angle of the knee unit 10 is 0°.

The magnetic sensor 62 provided at the lower link 18 outputs a detection value corresponding to the distance d to the magnet 60 provided at the upper link 16. The intensity of the magnetic field formed by the magnet 60 decreases as the distance from the magnet 60 increases. As illustrated in FIG. 2, when the bending angle of the knee unit 10 is 0°, the distance d between the magnet 60 and the magnetic sensor 62 is the smallest, and the detection value of the magnetic sensor 62 is the largest at this time. As illustrated in FIG. 3, as the bending angle of the knee unit 10 increases, the distance d increases, and thus the detection value of the magnetic sensor 62 decreases.

The multi-articulated link knee joint 100 further includes a control device 14. The control device 14 is accommodated in the lower leg part 12. The control device 14 receives a detection value of the relative position detector 58 (that is, a detection value of the magnetic sensor 62), obtains the bending angle of the knee unit 10 from the detection value, and controls an auxiliary driver (not illustrated).

Figure 4:
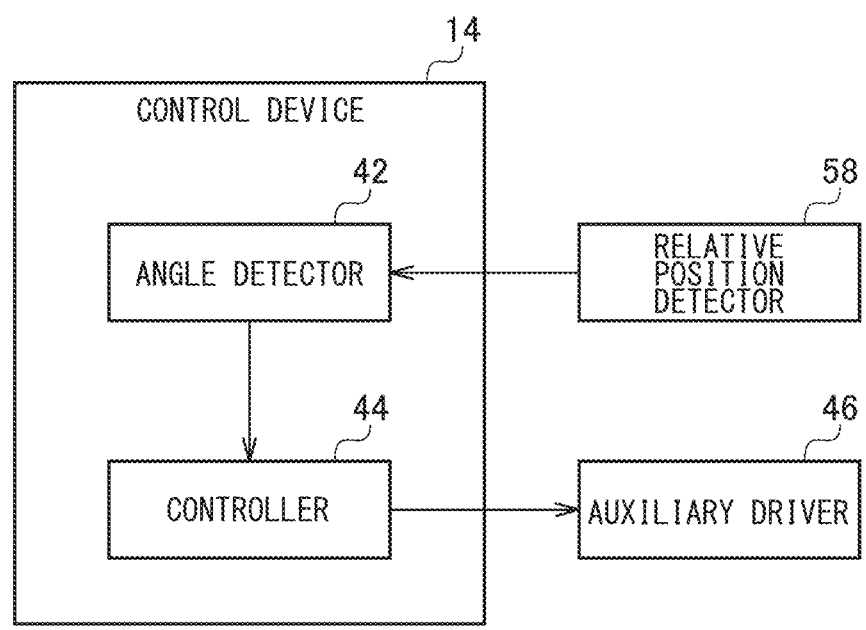
FIG. 4 is a block diagram illustrating a functional configuration of a control device.

FIG. 4 is a block diagram illustrating a functional configuration of the control device 14. Each of the blocks illustrated herein in the block diagram can be implemented by an element or a mechanical device including a CPU of a computer from the perspectives of hardware and, from the perspectives of software, by a computer program or the like. In this example, functional blocks implemented by coordination thereof are illustrated. Therefore, it should be understood by a person skilled in the art that these functional blocks can be implemented by various forms by hardware, software, or a combination thereof.

The control device 14 includes an angle detector 42 and a controller 44. The angle detector 42 obtains the bending angle of the knee unit 10 from a detection value of the relative position detector 58. For example, when a table is generated in advance by measuring the relationship between the bending angle of the knee unit 10 and the detection value of the relative position detector 58, a bending angle of the knee unit 10 can be obtained from a detection value of the relative position detector 58 by referring to the table.

The controller 44 controls an auxiliary driver 46 in accordance with the bending angle obtained by the angle detector 42. In the present embodiment, the auxiliary driver 46 is a rotary hydraulic damper attached to the first shaft 24 and is controlled by the controller 44 to assist the motion of the knee unit 10. The controller 44 controls the auxiliary driver 46 so as to limit the rotation of the third shaft 28 when the bending angle is close to 0°. This prevents knee bending, that is, the knee unit 10 bent against the will of the user. In addition, when the leg is in a swinging state in which the bending angle changes such as when walking, the auxiliary driver 46 is controlled so as to rotate the third shaft 28 in accordance with the angle-changing direction. As a result, the lower leg part 12 swings in accordance with kicking-out of the leg, and thus the user can walk comfortably. Note that the rotary hydraulic damper serving as the auxiliary driver 46 may be provided at any one of the second shaft 26, the third shaft 28, and the fourth shaft 30. However, since there are times that the rotation direction of the third shaft 28 and the fourth shaft 30 is reversed during rotation of the upper link 16, the rotary hydraulic damper is more easily controlled when provided at the first shaft 24 or the second shaft 26 that rotates always in the same direction as the upper link 16 does. Alternatively, a cylinder device such as an air cylinder or a hydraulic cylinder may be provided as the auxiliary driver 46.

The usage and operation according to the above configuration are as follows. The multi-articulated link knee joint 100 is used while the thigh connector 32 is connected to a socket attached to the thigh of the user with the leg part connected to the leg connector 40. The knee unit 10 bends when the upper link 16 rotates relative to the lower link 18 by the multi-articulated link mechanism. When the knee unit 10 is bent, the angle detector 42 obtains the bending angle from the detection value of the relative position detector 58. The controller 44 controls the auxiliary driver in accordance with the bending angle to assist the motion of the knee unit 10.

In the multi-articulated link knee joint 100 according to the first embodiment, since the relative position detector 58 including the magnet 60 and the magnetic sensor 62 is included in the knee unit 10, even with auxiliary drivers of different types, the bending angle of the knee unit 10 can be detected. In deploying various product groups, the configuration for detecting the bending angle can be shared to reduce the manufacturing cost.

In the multi-articulated link knee joint 100 according to the first embodiment, both the magnetic sensor 62 of the relative position detector 58 and the angle detector 42 (control device 14) are provided at the lower link unit 52. Since the angle detector 42 obtains the bending angle of the knee unit 10 from the detection result of the magnetic sensor 62, in order to transmit detection information of the magnetic sensor 62 to the angle detector 42, it is necessary that the magnetic sensor 62 and the angle detector 42 be connected by wiring. In the case where the magnetic sensor 62 and the angle detector 42 are provided at separate portions that are displaced from each other, it is necessary to adopt a structure that does not cause a failure such as disconnection in the wiring. This is not preferable since this leads to increased cost of the knee joint. In the multi-articulated link knee joint 100 according to the first embodiment, since the magnetic sensor 62 and the angle detector 42 (the control device 14) are provided at the same lower link unit 52, the wiring can be made simple, which results in cost reduction of the knee joint.

Second Embodiment

In the first embodiment, the relative position detector 58 detects the distance d between the magnet 60 provided at the upper link 16 and the magnetic sensor 62 provided at the lower link 18 and thereby detects the relative position of the upper link unit 50 relative to the lower link unit 52. However, the relative position detector 58 may not only detect the relative position of the upper link unit 50 relative to the lower link unit 52, but may also detect the relative position of another link unit relative to a certain link unit among the four link units. In a second embodiment, an example as such will be described.

Figure 5:
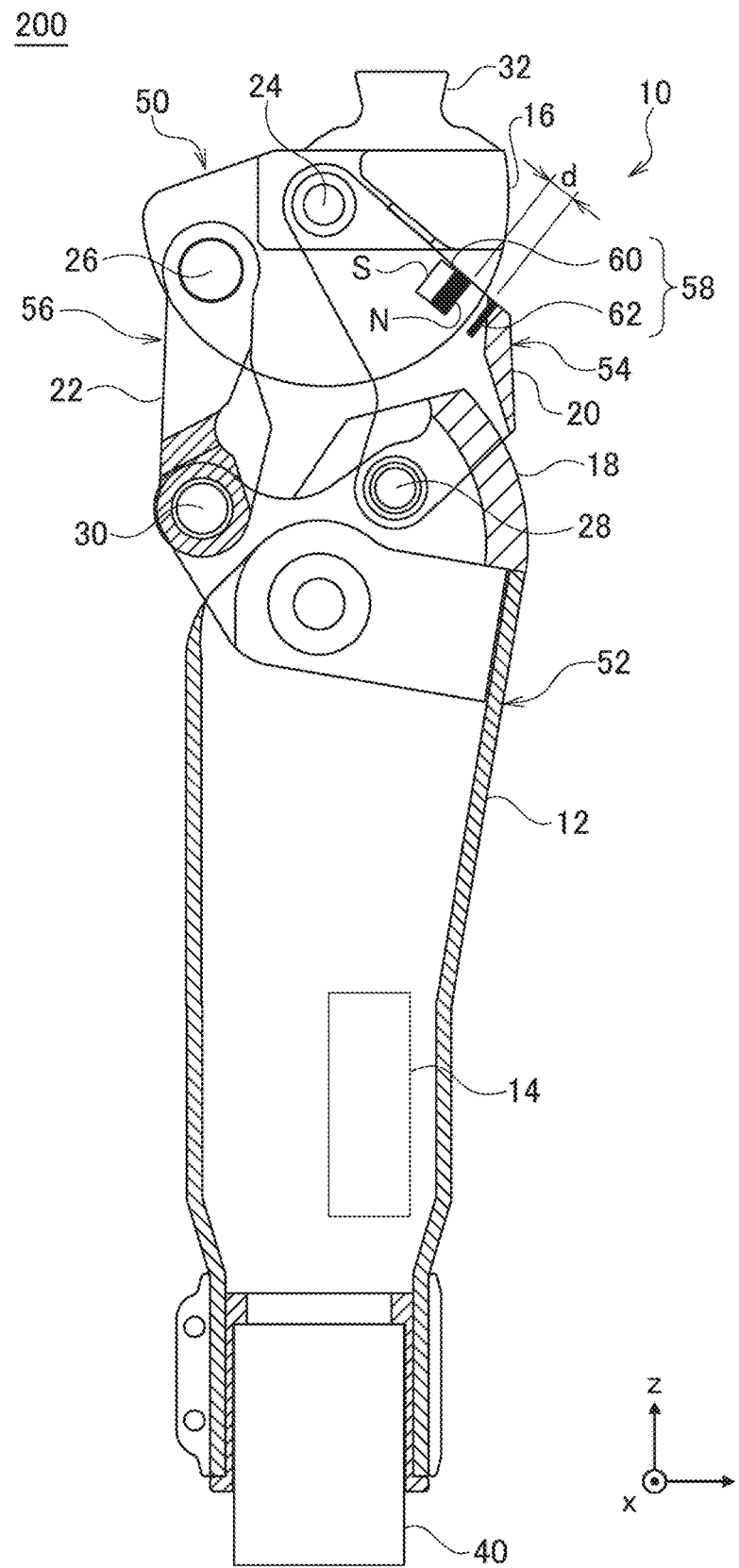
FIG. 5 is a schematic cross-sectional view of a multi-articulated link knee joint according to a second embodiment of the present invention.
Figure 6:
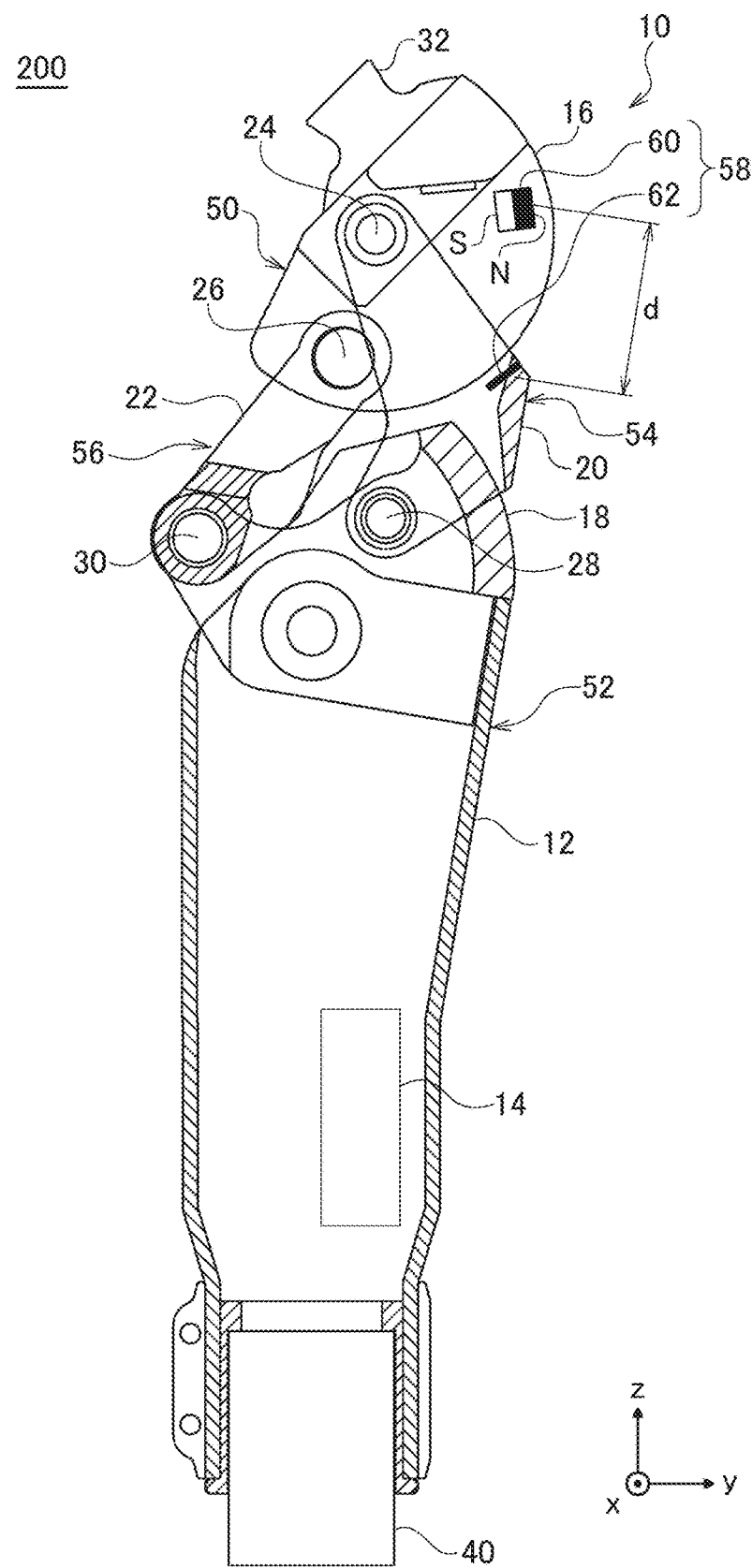
FIG. 6 is a view illustrating a state in which a knee unit is bent by 45° in the multi-articulated link knee joint according to the second embodiment.

FIG. 5 is a schematic cross-sectional view of a multi-articulated link knee joint 200 according to the second embodiment of the present invention. In the multi-articulated link knee joint 200 illustrated in FIG. 5, the bending angle of a knee unit 10 is 0°. FIG. 6 is a view illustrating a state in which the knee unit 10 is bent by 45° in the multi-articulated link knee joint 200 according to the second embodiment.

The multi-articulated link knee joint 200 differs from the multi-articulated link knee joint 100 according to the first embodiment in that a magnetic sensor 62 of a relative position detector 58 is provided at an anterior link 20. The magnet 60 is provided at a predetermined portion of the upper link 16, for example, at a portion that approaches close to the magnetic sensor 62 when the bending angle is 0°. Therefore, in the second embodiment, the relative position detector 58 including the magnet 60 and the magnetic sensor 62 detects the relative position of the upper link unit 50 relative to the anterior link unit 54.

The magnetic sensor 62 provided at the anterior link 20 outputs a detection value corresponding to the distance d to the magnet 60 provided at the upper link 16. The intensity of the magnetic field formed by the magnet 60 decreases as the distance from the magnet 60 increases. As illustrated in FIG. 5, when the bending angle of the knee unit 10 is 0°, the distance d between the magnet 60 and the magnetic sensor 62 is the smallest, and the detection value of the magnetic sensor 62 is the largest at this time. As illustrated in FIG. 6, as the bending angle of the knee unit 10 increases, the distance d increases, and thus the detection value of the magnetic sensor 62 decreases.

Also in the multi-articulated link knee joint 200 according to the second embodiment, the bending angle of the knee unit 10 is obtained on the basis of the detection value of the relative position detector 58, and an auxiliary driver (not illustrated) is controlled in accordance with the obtained bending angle. Since the relative position detector 58 including the magnet 60 and the magnetic sensor 62 is provided at the knee unit 10, even with auxiliary drivers of different types, the bending angle of the knee unit 10 can be detected.

Third Embodiment

Figure 7:
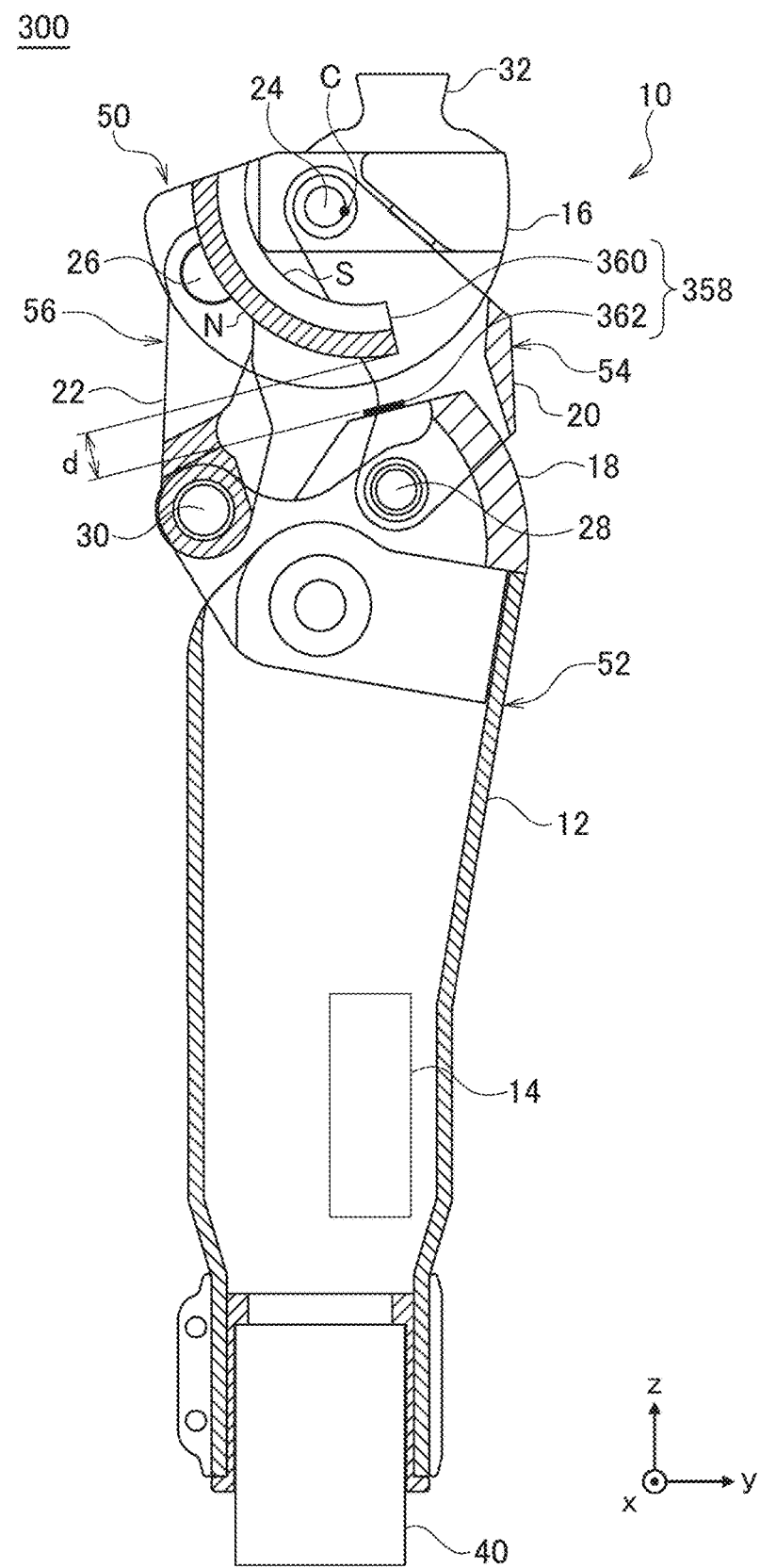
FIG. 7 is a schematic cross-sectional view of a multi-articulated link knee joint according to a third embodiment of the present invention.
Figure 8:
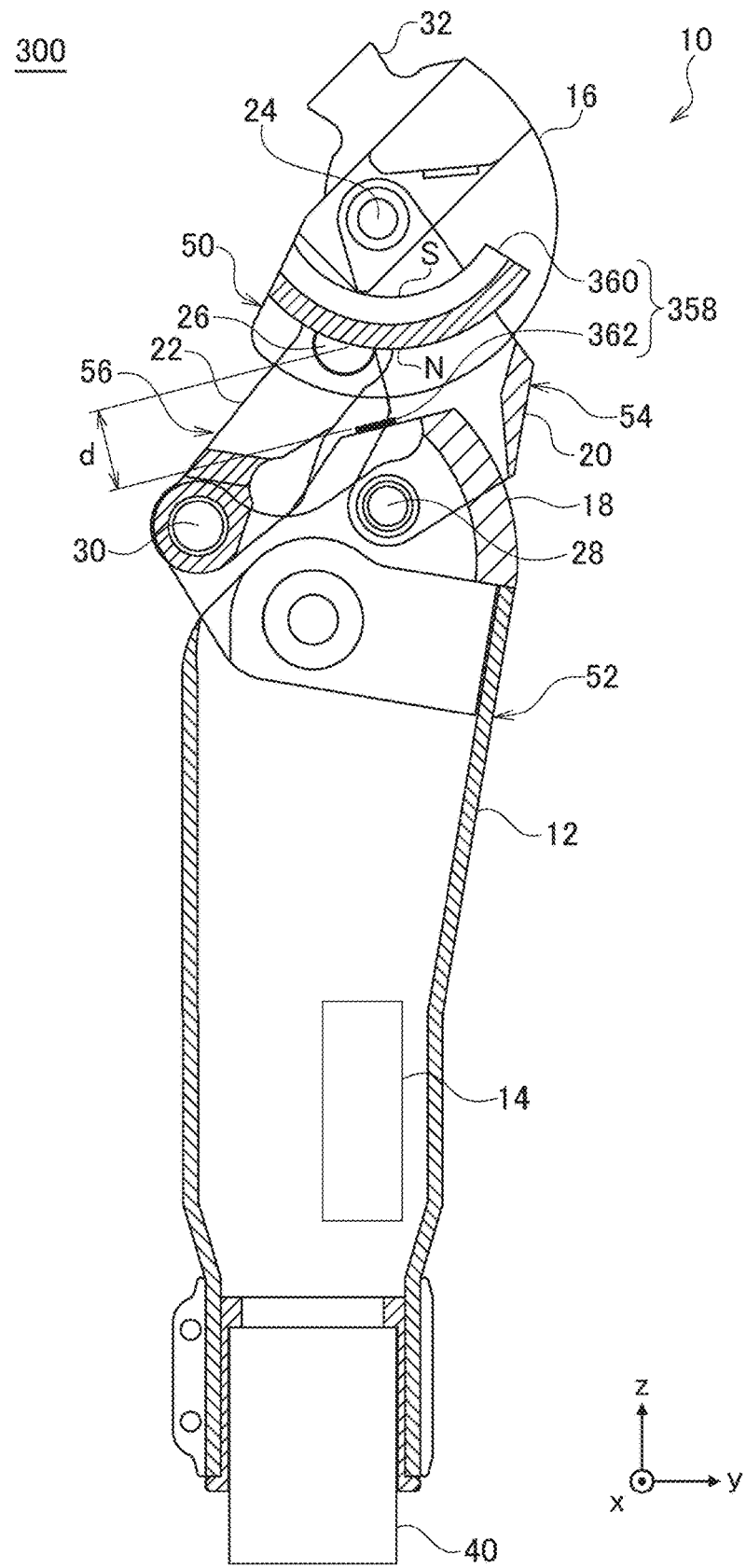
FIG. 8 is a view illustrating a state in which a knee unit is bent by 45° in the multi-articulated link knee joint according to the third embodiment.

FIG. 7 is a schematic cross-sectional view of a multi-articulated link knee joint 300 according to a third embodiment of the present invention. In the multi-articulated link knee joint 300 illustrated in FIG. 7, the bending angle of a knee unit 10 is 0°. FIG. 8 is a view illustrating a state in which the knee unit 10 is bent by 45° in the multi-articulated link knee joint 300 according to the third embodiment.

The multi-articulated link knee joint 300 is different from the multi-articulated link knee joint 100 according to the first embodiment in the structure of the relative position detector. A relative position detector 358 of the multi-articulated link knee joint 300 includes a magnet 360 and a magnetic sensor 362 that detects the intensity of the magnetic field generated by the magnet 360. The magnetic sensor 362 may be, for example, a Hall element. The magnetic sensor 362 is provided at a predetermined portion of a lower link 18, for example, on the lower link 18.

In the third embodiment, the magnet 360 is a bar magnet extending in an arc shape in the rotation direction of an upper link 16. The magnet 360 is arranged such that the N pole faces the magnetic sensor 362 and the S pole faces the opposite side to the magnetic sensor 362. In FIG. 7, symbol "C" indicates the center of the magnet 360 extending in the arc shape. The center C of the arc-shaped magnet 360 is eccentric anteriorly with respect to the center of a first shaft 24 which is the rotation axis of the upper link 16, and thus the distance d between the magnet 360 and the magnetic sensor 362 varies as the bending angle of the knee unit 10 varies.

The magnetic sensor 362 provided at the lower link 18 outputs a detection value corresponding to the distance d to the magnet 360 provided at the upper link 16. The intensity of the magnetic field formed by the magnet 360 decreases as the distance from the magnet 360 increases. As illustrated in FIG. 7, when the bending angle of the knee unit 10 is 0°, the distance d is the smallest, and the detection value of the magnetic sensor 362 is the largest at this time. As illustrated in FIG. 8, as the bending angle of the knee unit 10 increases, the distance d increases, and thus the detection value of the magnetic sensor 362 decreases.

Also in the multi-articulated link knee joint 300 according to the third embodiment, the bending angle of the knee unit 10 is obtained on the basis of the detection value of the relative position detector 358, and an auxiliary driver (not illustrated) is controlled in accordance with the obtained bending angle. Since the relative position detector 358 including the magnet 360 and the magnetic sensor 362 is provided at the knee unit 10, even with auxiliary drivers of different types, the bending angle of the knee unit 10 can be detected.

In the multi-articulated link knee joint 300 according to the third embodiment, since the magnetic sensor 362 and an angle detector (control device 14) are provided at the same lower link unit 52, the wiring can be made simple, which results in cost reduction of the knee joint.

Moreover, in the multi-articulated link knee joint 300 according to the third embodiment, the arc-shaped bar magnet is adopted as the magnetic sensor 362 in the relative position detector 358. Therefore, as compared with the case where the square magnet 60 is used as in the first and second embodiments described above, a strong magnetic field can be formed around the magnetic sensor 362 even when the bending angle increases. As a result, the detection accuracy of the relative position detector 358 can be enhanced as compared with the first and second embodiments, and moreover, the detection range of the bending angle can be broadened.

Fourth Embodiment

Figure 9:
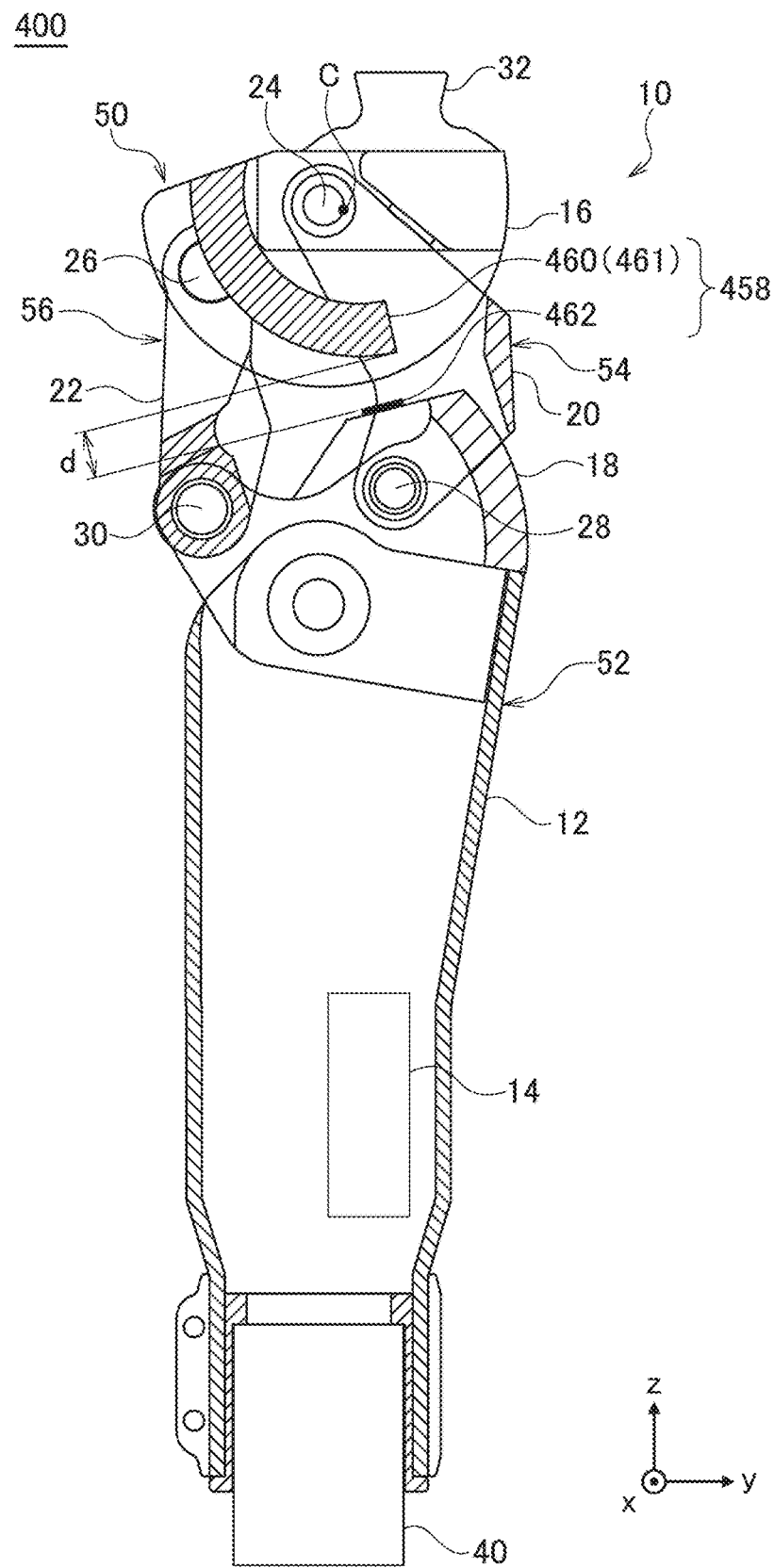
FIG. 9 is a schematic cross-sectional view of a multi-articulated link knee joint according to a fourth embodiment of the present invention.
Figure 10:
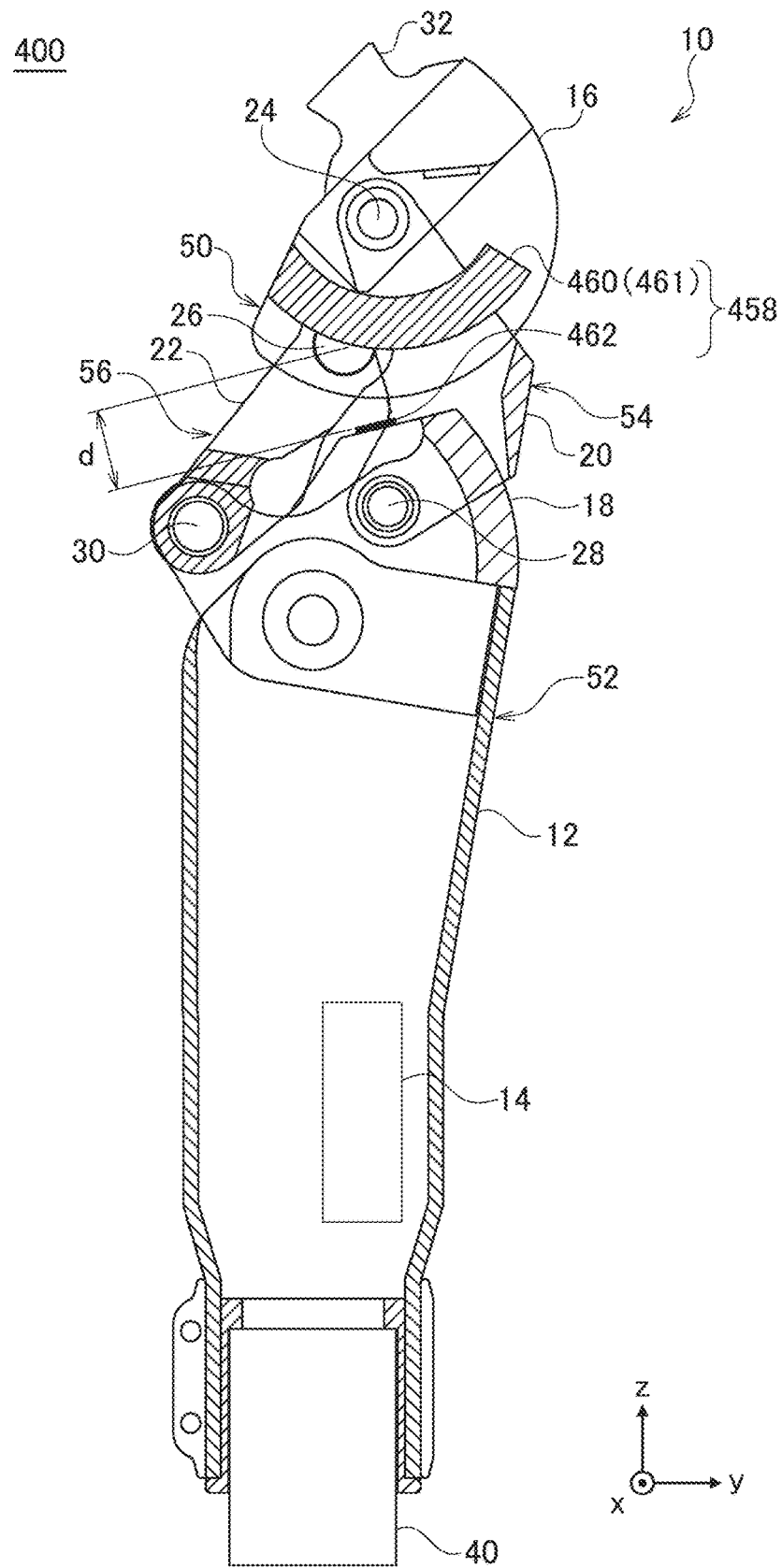
FIG. 10 is a view illustrating a state in which a knee unit is bent by 45° in the multi-articulated link knee joint according to the fourth embodiment.

FIG. 9 is a schematic cross-sectional view of a multi-articulated link knee joint 400 according to a fourth embodiment of the present invention. In the multi-articulated link knee joint 400 illustrated in FIG. 9, the bending angle of a knee unit 10 is 0°. FIG. 10 is a view illustrating a state in which the knee unit 10 is bent by 45° in the multi-articulated link knee joint 400 according to the fourth embodiment.

Figure 11:
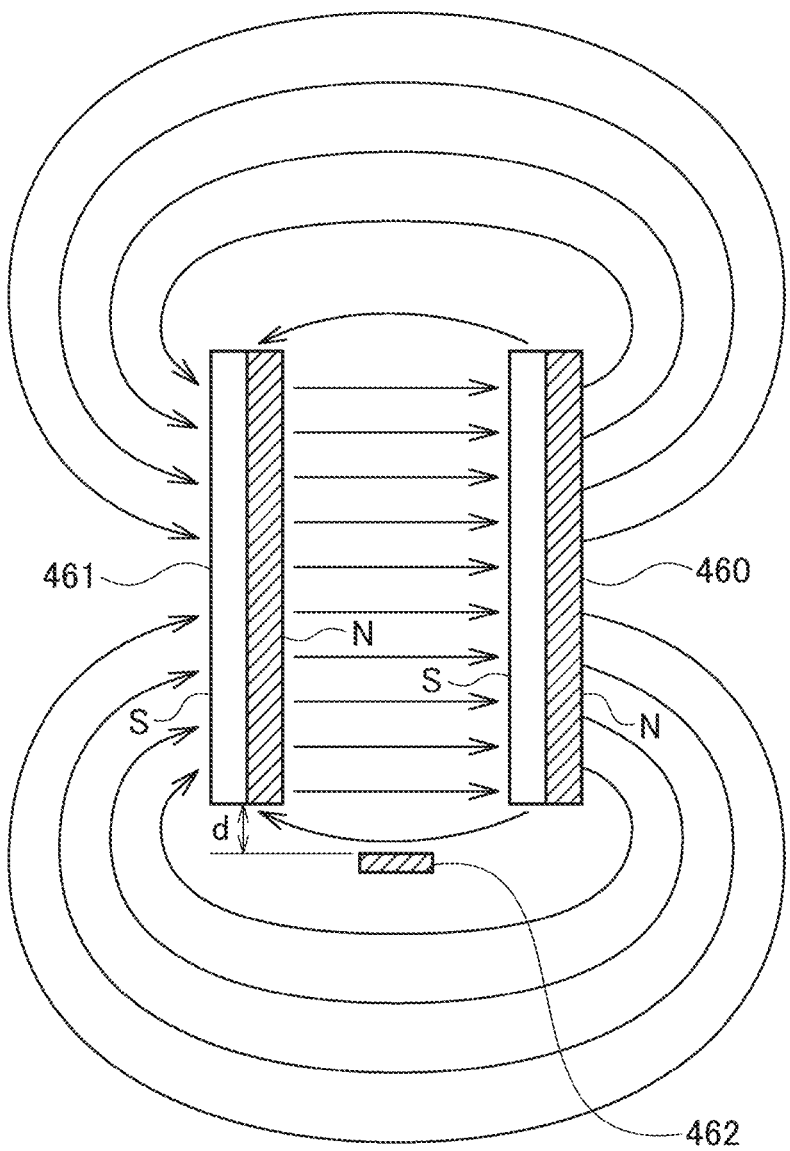
FIG. 11 is a diagram for explaining a structure of a relative position detector in the multi-articulated link knee joint according to the fourth embodiment.

The multi-articulated link knee joint 400 also differs from the multi-articulated link knee joint 100 according to the first embodiment in the structure of the relative position detector. FIG. 11 is a diagram for explaining a structure of a relative position detector 458 in the multi-articulated link knee joint 400 according to the fourth embodiment. The relative position detector 458 includes a first magnet 460, a second magnet 461, and a magnetic sensor 462 that detects the intensity of the magnetic field generated by the first magnet 460 and the second magnet 461, and detects the relative position of an upper link unit 50 relative to the lower link unit 52. The magnetic sensor 462 may be, for example, a Hall element. The magnetic sensor 462 is provided at a predetermined portion of a lower link 18, for example, on the lower link 18.

The first magnet 460 and the second magnet 461 are bar magnets extending in an arc shape in the rotation direction of an upper link 16. As illustrated in FIG. 9, the center C of the arc-shaped first magnet 460 and the second magnet 461 is eccentric anteriorly with respect to the center of a first shaft 24 which is the rotation axis of the upper link 16, and thus the distance d between the first magnet 460 and the second magnet 461 and the magnetic sensor 462 varies as the bending angle of the knee unit 10 varies.

As illustrated in FIG. 11, the first magnet 460 and the second magnet 461 are arranged such that the S pole of the first magnet 460 and the N pole of the second magnet 461 face each other. In FIG. 11, the magnetic field formed by the first magnet 460 and the second magnet 461 is illustrated. The intensity of the magnetic field formed by the first magnet 460 and the second magnet 461 decreases as the distance from the first magnet 460 and the second magnet 461 increases. As illustrated in FIG. 9, when the bending angle of the knee unit 10 is 0°, the distance d is the smallest, and the detection value of the magnetic sensor 462 is the largest at this time. As illustrated in FIG. 10, as the bending angle of the knee unit 10 increases, the distance d increases, and thus the detection value of the magnetic sensor 462 decreases.

Also in the multi-articulated link knee joint 400 according to the fourth embodiment, the bending angle of the knee unit 10 is obtained on the basis of the detection value of the relative position detector 358, and an auxiliary driver (not illustrated) is controlled in accordance with the obtained bending angle. Since the relative position detector 458 including the first magnet 460, the second magnet 461, and the magnetic sensor 462 is provided at the knee unit 10, even with auxiliary drivers of different types, the bending angle of the knee unit 10 can be detected.

In the multi-articulated link knee joint 400 according to the fourth embodiment, since the magnetic sensor 462 and an angle detector (control device 14) are provided at the same lower link unit 52, the wiring can be made simple, which results in cost reduction of the knee joint.

Furthermore, in the multi-articulated link knee joint 400 according to the fourth embodiment, the first magnet 460 and the second magnet 461 are arranged to face each other in the relative position detector 458, which allows an even stronger magnetic field to be formed as compared with the case of using the single magnet 360 as in the third embodiment described above. As a result, the detection accuracy of the relative position detector 458 can be further enhanced as compared with the third embodiment, and moreover, the detection range of the bending angle can be broadened.

Fifth Embodiment

Figure 12:
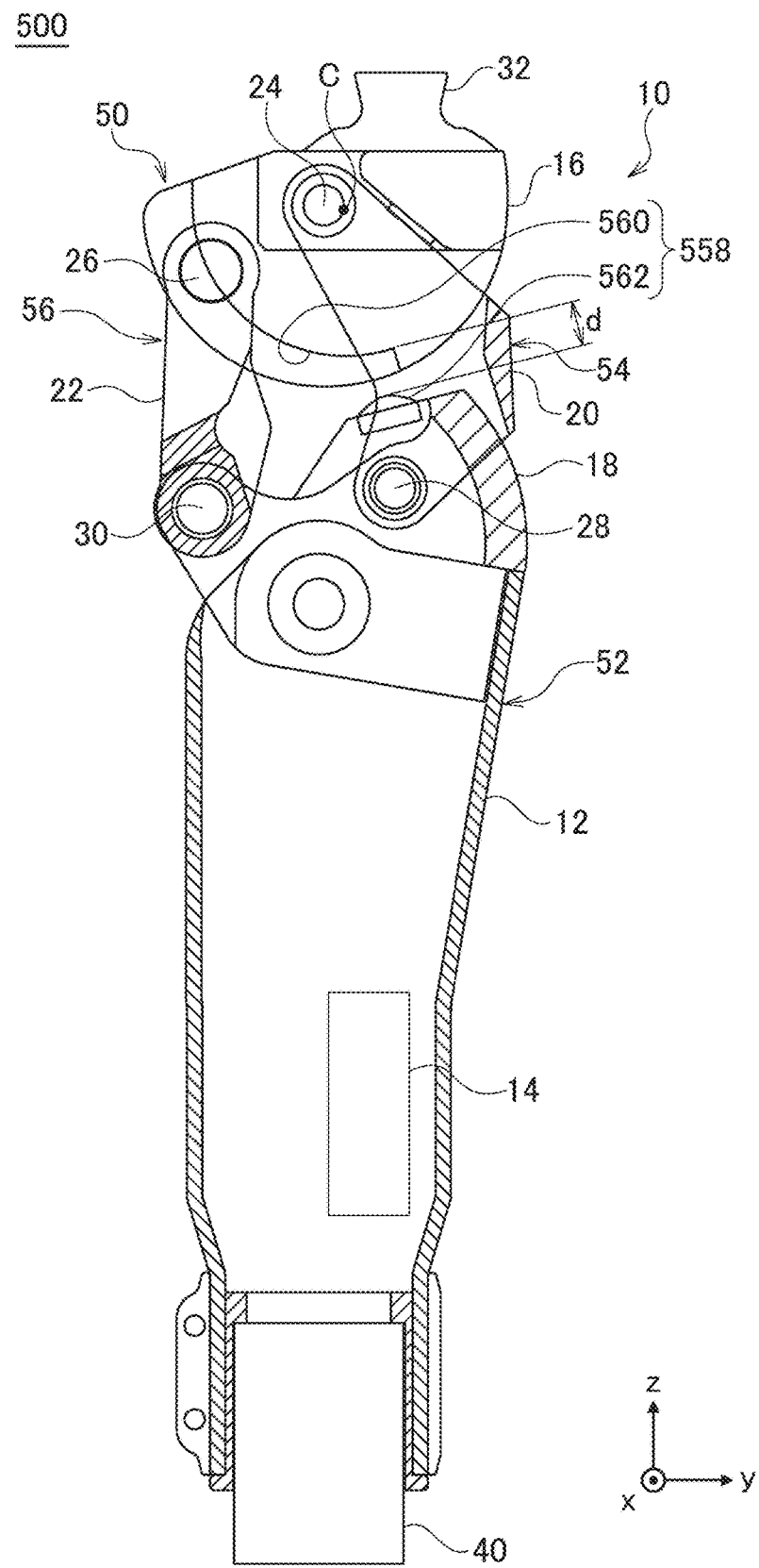
FIG. 12 is a schematic cross-sectional view of a multi-articulated link knee joint according to a fifth embodiment of the present invention.

FIG. 12 is a schematic cross-sectional view of a multi-articulated link knee joint 500 according to a fifth embodiment of the present invention. In the multi-articulated link knee joint 500 illustrated in FIG. 12, the bending angle of a knee unit 10 is 0°.

The multi-articulated link knee joint 500 is different from the multi-articulated link knee joint 100 according to the first embodiment in the structure of the relative position detector. A relative position detector 558 of the multi-articulated link knee joint 500 includes a groove 560 formed in an upper link 16 and a distance sensor 562 provided at a lower link 18. The relative position detector 558 detects the relative position of an upper link unit 50 relative to a lower link unit 52.

The groove 560 is formed on the outer circumferential surface of the upper link 16 on the lower link 18 side so as to extend in an arc shape along the rotation direction of the upper link 16. The groove 560 is formed such that the depth varies along the extending direction. In FIG. 12, symbol "C" indicates the center of the groove 560 extending in an arc shape. As illustrated in FIG. 12, the center C of the groove 560 is eccentric anteriorly with respect to the center of a first shaft 24 which is the rotation axis of the upper link 16. With this structure, when the bending angle of the knee unit 10 is 0°, the depth of the groove 560 increases as it extends posteriorly.

The distance sensor 562 detects the distance d to the bottom of the groove 560, and may be, for example, an infrared sensor or an ultrasonic sensor. Since the depth of the groove 560 increases as it extends posteriorly as described above, the detection value of the distance sensor 562 (that is, distance d) is the smallest when the bending angle of the knee unit 10 is 0° as illustrated in FIG. 12, and the detection value of the distance sensor 562 increases when the bending angle of the knee unit 10 increases.

An angle detector 42 (see FIG. 4) of the control device 14 obtains the bending angle of the knee unit 10 from the detection value of the relative position detector 558 (that is, the detection value of the distance sensor 562). For example, when a table is generated in advance by measuring the relationship between the bending angle of the knee unit 10 and the detection value of the relative position detector 558, a bending angle of the knee unit 10 can be obtained from a detection value of the relative position detector 558 by referring to the table.

Also in the multi-articulated link knee joint 500 according to the fifth embodiment, the bending angle of the knee unit 10 is obtained on the basis of the detection value of the relative position detector 558, and an auxiliary driver (not illustrated) is controlled in accordance with the obtained bending angle. Since the relative position detector 558 including the groove 560 and the distance sensor 562 is provided at the knee unit 10, even with auxiliary drivers of different types, the bending angle of the knee unit 10 can be detected.

In the multi-articulated link knee joint 500 according to the fifth embodiment, since the distance sensor 562 and an angle detector (control device 14) are provided at the same lower link unit 52, the wiring can be made simple, which results in cost reduction of the knee joint.

Sixth Embodiment

Figure 13:
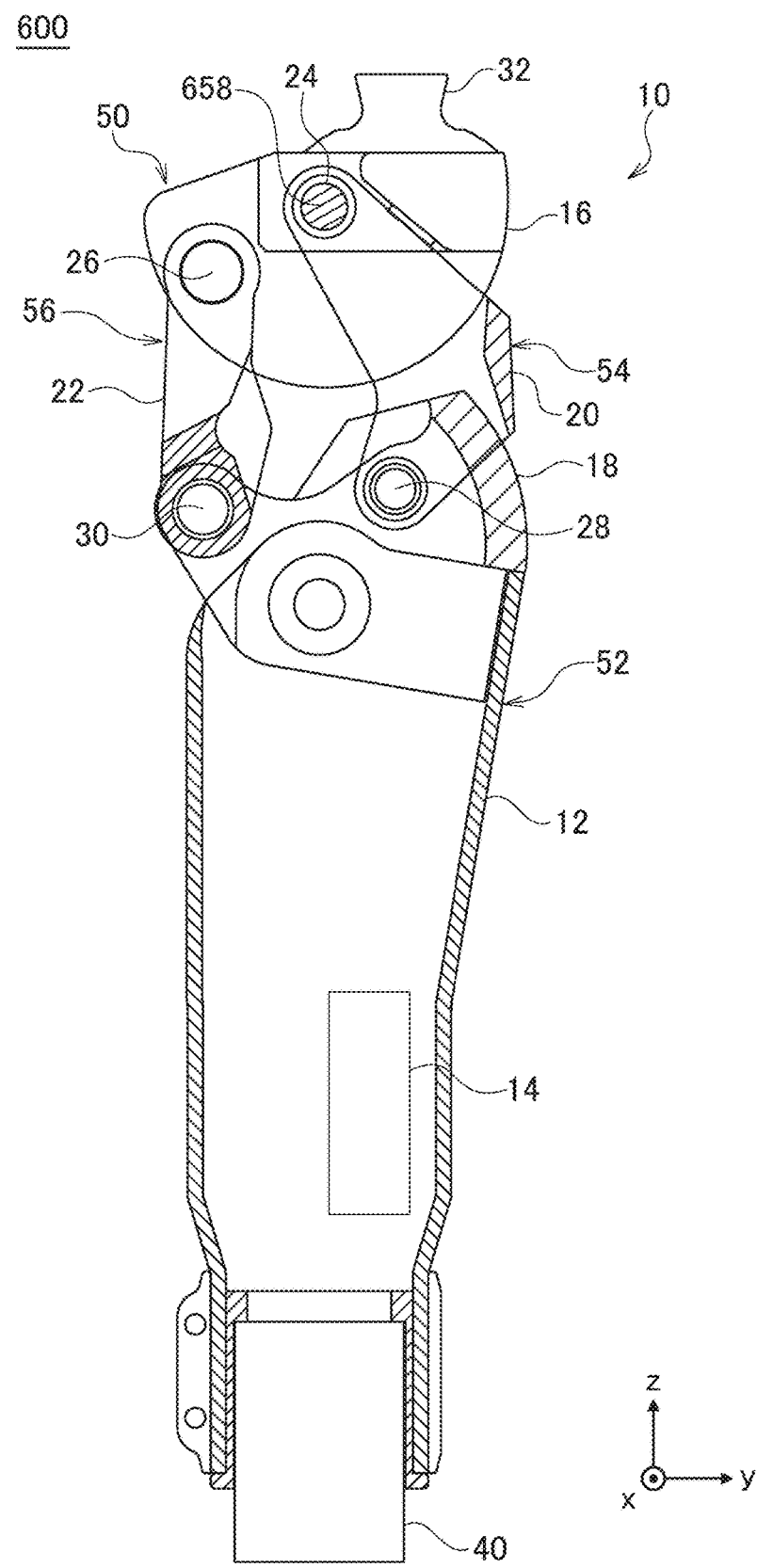
FIG. 13 is a schematic cross-sectional view of a multi-articulated link knee joint according to a sixth embodiment of the present invention.

FIG. 13 is a schematic cross-sectional view of a multi-articulated link knee joint 600 according to a sixth embodiment of the present invention. In the multi-articulated link knee joint 600 illustrated in FIG. 13, the bending angle of a knee unit 10 is 0°. Unlike the above embodiments, in the multi-articulated link knee joint 600 according to the sixth embodiment, the rotation angle of an upper link unit 50 with respect to an anterior link unit 54 (that is, rotation angle about a first shaft 24) is detected, and the bending angle of the knee unit 10 is obtained on the basis of the detection result.

The multi-articulated link knee joint 600 includes an angle sensor 658 that detects the rotation angle about the first shaft 24 of the upper link 16 as a relative position detector. The angle sensor 658 is provided at a first shaft 24. As the angle sensor 658, for example, a potentiometer, a rotary encoder, a resolver, or the like can be used.

Figure 14:
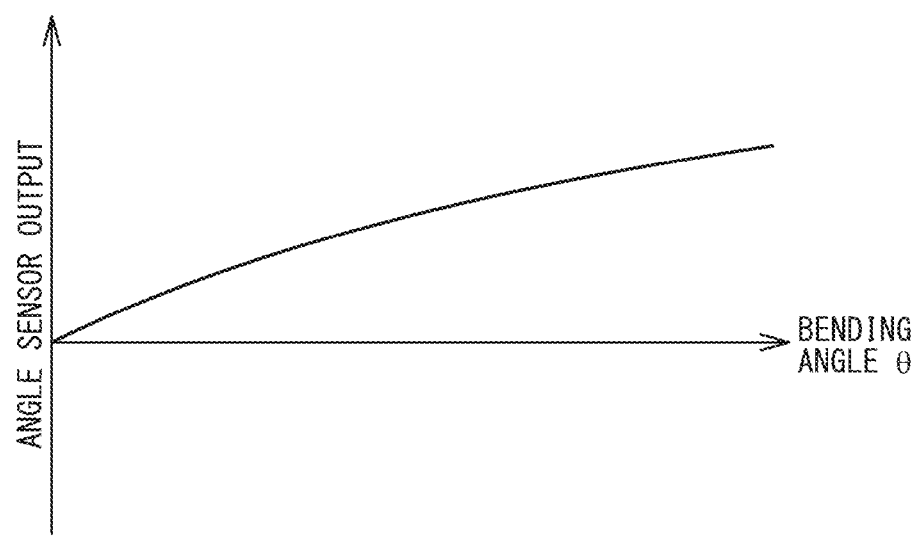
FIG. 14 is a graph illustrating an exemplary relationship between the bending angle of a knee unit and the output of an angle sensor.

FIG. 14 illustrates an example of the relationship between the bending angle θ of the knee unit 10 and the output (detection value) of the angle sensor 658. In the example illustrated in FIG. 14, as the bending angle θ of the knee unit 10 increases, the output of the angle sensor also increases. Since the bending angle θ of the knee unit 10 and the output of the angle sensor 658 correspond on one-to-one basis, the bending angle of the knee unit 10 can be obtained from the output of the angle sensor 658. Then, an auxiliary driver (not illustrated) is controlled in accordance with the obtained bending angle of the knee unit 10.

Also in the multi-articulated link knee joint 600 according to the sixth embodiment, since the angle sensor 658 as the relative position detector is provided at the knee unit 10, even with auxiliary drivers of different types, the bending angle of the knee unit 10 can be detected.

In the sixth embodiment, the angle sensor 658 is provided at the first shaft 24; however, an angle sensor may be provided at a second shaft 26 to detect the rotation angle of the upper link unit 50 with respect to a posterior link unit 56 (that is, rotation angle about the second shaft 26) may be detected. Even in the case where an angle sensor is provided at the second shaft 26, the bending angle θ of the knee unit 10 and the output of the angle sensor correspond on one-to-one basis, and thus the bending angle of the knee unit 10 can be obtained from the output of the angle sensor.

Seventh Embodiment

Figure 15:
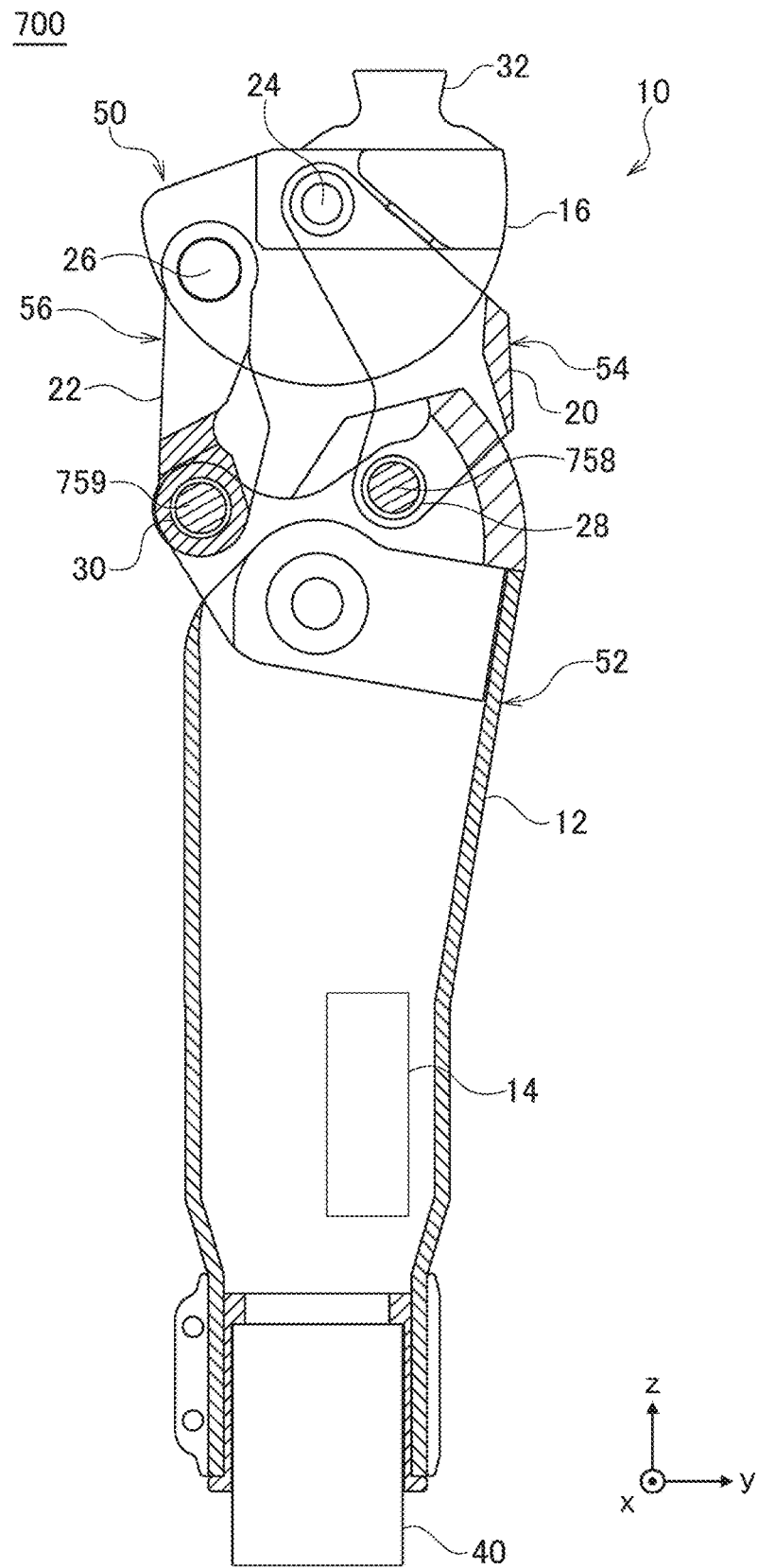
FIG. 15 is a schematic cross-sectional view of a multi-articulated link knee joint according to a seventh embodiment of the present invention.

FIG. 15 is a schematic cross-sectional view of a multi-articulated link knee joint 700 according to a seventh embodiment of the present invention. In the multi-articulated link knee joint 700 illustrated in FIG. 15, the bending angle of the knee unit 10 is 0°. In the multi-articulated link knee joint 700 according to the seventh embodiment, rotation angles of an anterior link unit 54 and a posterior link unit 56 with respect to a lower link unit 52 (that is, rotation angles about a third shaft 28 and a fourth shaft 30) are detected, and the bending angle of the knee unit 10 is detected on the basis of the detection results.

The multi-articulated link knee joint 700 includes, as a relative position detector, a first angle sensor 758 for detecting the rotation angle of an anterior link 20 about the third shaft 28 and a second angle sensor 759 for detecting the rotation angle about the fourth shaft 30 of a posterior link 22. The first angle sensor 758 is provided at the third shaft 28, and the second angle sensor 759 is provided at the fourth shaft 30. As the first angle sensor 758 and the second angle sensor 759, for example, potentiometers, rotary encoders, resolvers, or the like can be used.

In the multi-articulated link knee joint 700 according to the seventh embodiment, an angle detector 42 (see FIG. 4) of the control device 14 obtains the bending angle on the basis of the output of the first angle sensor 758 and the second angle sensor 759.

Figure 16:
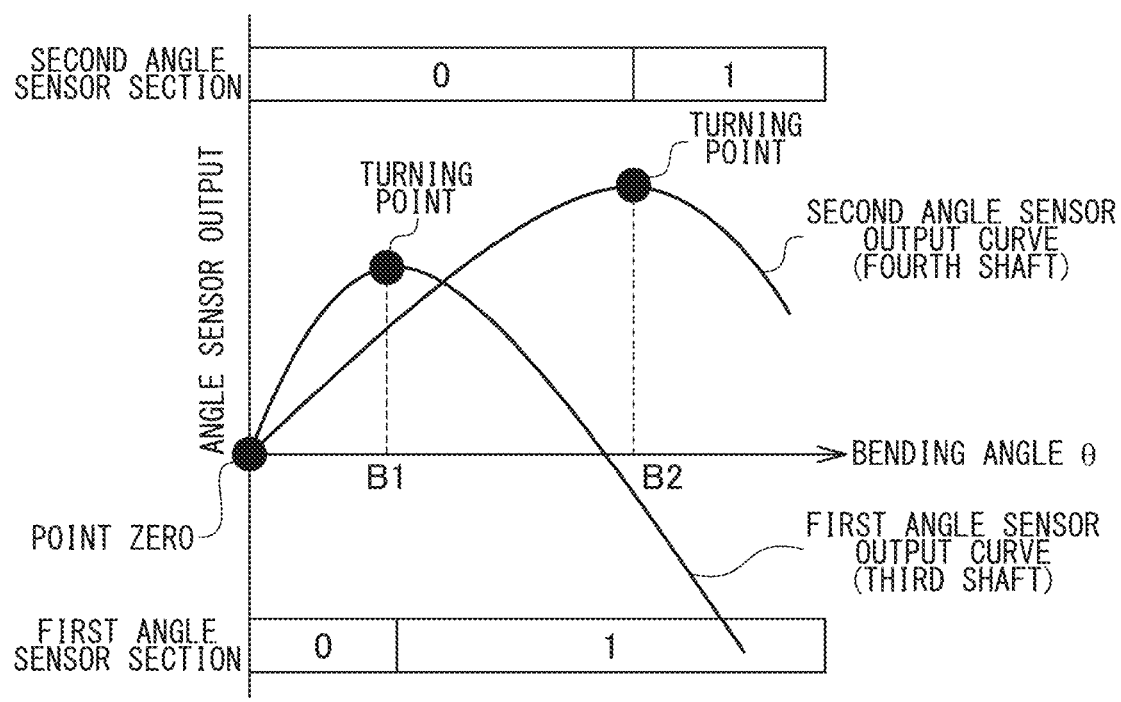
FIG. 16 is a graph illustrating an exemplary relationship between the bending angle of a knee unit and the output of a first angle sensor and a second angle sensor.

FIG. 16 illustrates an example of the relationship between the bending angle θ of the knee unit 10 and the output (detection values) of the first angle sensor 758 and the second angle sensor 759. In a first shaft 24 and a second shaft 26 provided at an upper link 16 in a four-articulated link mechanism, the output of an angle sensor and the bending angle of a knee unit 10 correspond on one-to-one basis; however in a third shaft 28 and a fourth shaft 30 provided to a lower link 18, the output of the angle sensor and the bending angle of the knee unit 10 do not correspond on one-to-one basis. That is, in the third shaft 28 and the fourth shaft 30, there are two different bending angles for the same angle sensor output. As illustrated in FIG. 16, an output curve of the first angle sensor 758 provided at the third shaft 28 has a turning point at a bending angle of θ=B1, and the second angle sensor 759 provided at the fourth shaft 30 has a turning point at a bending angle of θ=B2. This is because the four-articulated link mechanism reaches a dead point as deformation progresses, and then each of the links move in different directions. Therefore, it is difficult to obtain the bending angle only from the output of the first angle sensor 758 or only from the output of the second angle sensor 759. Therefore, in the seventh embodiment, the bending angle is obtained utilizing both the first angle sensor 758 and the second angle sensor 759.

Hereinafter, a method of obtaining the bending angle θ using the output of the first angle sensor 758 and the output of the second angle sensor 759 will be described. Let an angle sensor output when the bending angle θ of the knee unit 10 is 0° be the point zero. Each of the output curves of the first angle sensor 758 and the second angle sensor 759 is divided into a section (let this be section "0") having a bending angle smaller than the turning point and a section having a bending angle larger than the turning point (let this be section "1") (see FIG. 16).

FIG. 17 is a table illustrating combinations of the sections of the first angle sensor 758 and the sections of the second angle sensor 759. By combining the sections "0" and "1" of the first angle sensor 758 and the sections "0" and "1" of the second angle sensor 759, the following three groups are formed. For each of the groups, a relational expression of the angle sensor output and the bending angle θ is given.

(1) Group of θ<B1 (section "0" for the first angle sensor 758 and section "0" for the second angle sensor 759)

(2) Group of B1<θ<B2 (section "1" for the first angle sensor 758 and section "0" for the second angle sensor 759)

(3) Group of B2<θ (section "1" for the first angle sensor 758 and section "1" for the second angle sensor 759)

At the time of actual control, an angle detector 42 (see FIG. 4) of a control device 14 determines from the output of the first angle sensor 758 and the second angle sensor 759 which one of the above three groups the bending angle θ belongs to.

Figure 18A:
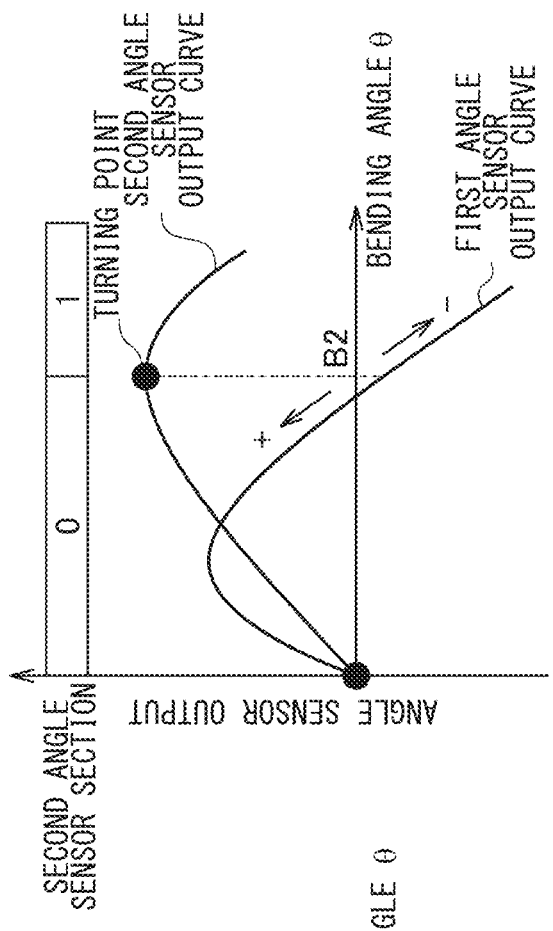
FIG. 18A and FIG. 18B are graphs for explaining a method of determining sections by a turning point.
Figure 18B:
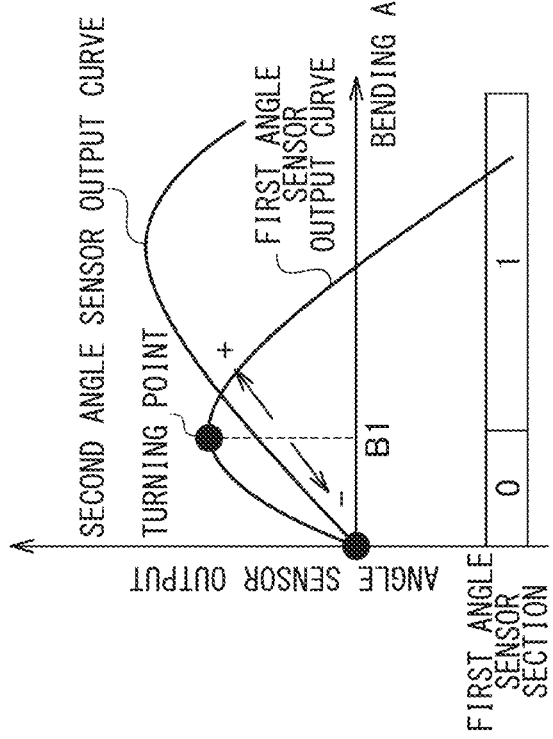

FIG. 18A and FIG. 18B are graphs for explaining a method of determining sections by a turning point. When the output of the first angle sensor 758 reaches the turning point (the point where the output changes from an increase to a decrease or from a decrease to an increase), a section for the first angle sensor 758 is determined from an increase/decrease of the second angle sensor 759. For example in FIG. 18A, in the case where the first angle sensor 758 has a decrease near the turning point and the second angle sensor 759 has an increase, section "1" is obtained for the first angle sensor 758, and section "0" is obtained for the second angle sensor 759. Thus, it can be determined that the bending angle belongs to the group of B1<θ<B2.

Moreover, when the output of the second angle sensor 759 reaches the turning point, a section for the second angle sensor 759 is determined from an increase/decrease of the first angle sensor 758. For example in FIG. 18B, in the case where the second angle sensor 759 has a decrease near the turning point and the first angle sensor 758 has an increase, section "1" is obtained for the first angle sensor 758, and section "1" is obtained for the second angle sensor 759. Thus, it can be determined that the bending angle belongs to the group of B2<θ.

After determining the group to which the bending angle θ belongs, the angle detector 42 obtains the bending angle θ using the relational expression between the angle sensor output given to the group to which the bending angle θ belongs and the bending angle θ. As described above, by determining the group to which the bending angle θ belongs and applying different relational expressions for each of the groups, the bending angle can be obtained even with the first angle sensor 758 and the second angle sensor 759 output of which having turning points It is desirable that the "point zero" of the angle sensor output described above be determined on the basis of the second angle sensor 759. As understood from FIG. 16, since for the first angle sensor 758 there is another bending angle θ, at which the same output value as that of the point zero is obtained, other than the bending angle of θ=0°, the point at which the bending angle θ equals 0° cannot be determined. On the other hand, since for the second angle sensor 759 there is no bending angle θ, at which the same output value as that of the point zero is obtained, other than the bending angle of θ=0°, the point at which the bending angle θ equals 0° can be determined uniquely.

Also in the multi-articulated link knee joint 700 according to the seventh embodiment, an auxiliary driver (not illustrated) is controlled in accordance with the obtained bending angle. Since the first angle sensor 758 and the second angle sensor 759 as the relative position detector are provided at the knee unit 10, even with auxiliary drivers of different types, the bending angle of the knee unit 10 can be detected.

In the multi-articulated link knee joint 700 according to the seventh embodiment, since the first angle sensor 758, the second angle sensor 759, and the angle detector (control device 14) are provided at the same lower link unit 52, the wiring can be made simple, which results in cost reduction of the knee joint.

Eighth Embodiment

Figure 19:
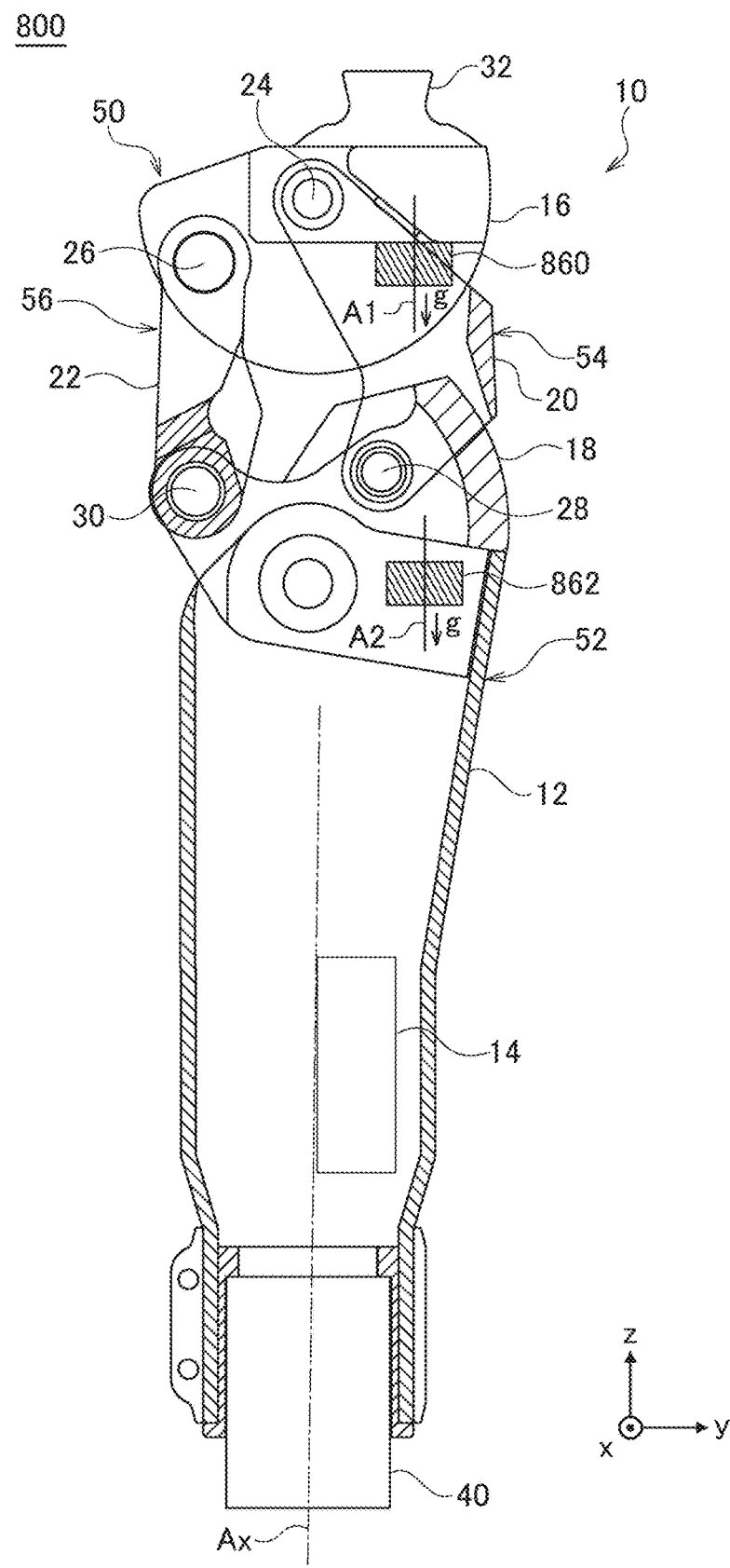
FIG. 19 is a schematic cross-sectional view of a multi-articulated link knee joint according to an eighth embodiment of the present invention.

FIG. 19 is a schematic cross-sectional view of a multi-articulated link knee joint 800 according to an eighth embodiment of the present invention. In the multi-articulated link knee joint 800 illustrated in FIG. 19, the bending angle of the knee unit 10 is 0°. The multi-articulated link knee joint 800 according to the seventh embodiment includes a first acceleration sensor 860 and a second acceleration sensor 862 as a relative position detector. The first acceleration sensor 860 is provided at an upper link 16, and the second acceleration sensor 862 is provided at a lower link 18. In the eighth embodiment, the relative position of an upper link unit 50 relative to a lower link unit 52 is detected using the first acceleration sensor 860 and the second acceleration sensor 862.

The first acceleration sensor 860 has a reference axis A1 and detects an angle Φ1 formed between the reference axis A1 and a direction of the gravitational acceleration g (vertical direction). When the bending angle of the knee unit 10 is 0° and the central axis Ax of an lower leg part 12 is parallel to the vertical direction, the first acceleration sensor 860 is arranged such that the reference axis A1 is oriented in the vertical direction. At this time, the angle Φ1 detected by the first acceleration sensor 860 is 0°. Similarly, the second acceleration sensor 862 has a reference axis A2 and detects an angle Φ2 formed between the reference axis A2 and a direction of the gravitational acceleration g (vertical direction). When the bending angle of the knee unit 10 is 0° and the central axis Ax of the lower leg part 12 is parallel to the vertical direction, the second acceleration sensor 862 is arranged such that the reference axis A2 is oriented in the vertical direction. At this time, the angle Φ2 detected by the second acceleration sensor 862 is 0°.

Figure 20:
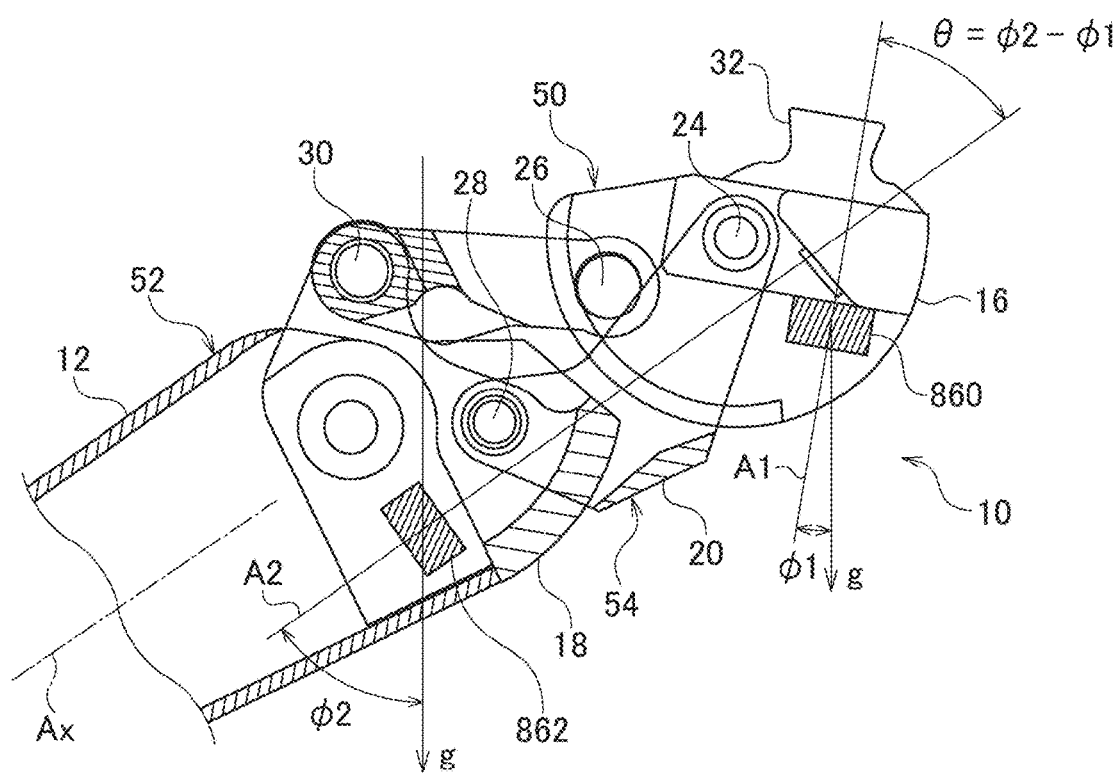
FIG. 20 is a view illustrating a state in which a knee unit is bent by 45° in the multi-articulated link knee joint according to the eighth embodiment.

FIG. 20 is a view illustrating a state in which the knee unit 10 is bent by 45° in the multi-articulated link knee joint 800 according to the eighth embodiment. FIG. 20 illustrates a state of the multi-articulated link knee joint 800 during walking, and the central axis Ax of the lower leg part 12 is inclined with respect to the vertical direction.

In the state illustrated in FIG. 20, the first acceleration sensor 860 provided at the upper link 16 detects an angle Φ1 formed between the reference axis A1 and the vertical direction. In addition, the second acceleration sensor 862 provided at the lower link 18 detects an angle Φ2 formed between the reference axis A2 and the vertical direction. The information of the angles Φ1 and Φ2 detected by the first acceleration sensor 860 and the second acceleration sensor 862 is sent to a control device 14. An angle detector 42 (see FIG. 4) of the control device 14 obtains the bending angle θ of the knee unit 10 on the basis of the angles Φ1 and Φ2. As can be seen from FIG. 20, the bending angle θ is obtained from the following mathematical formula:

$$\theta = \varphi 2 - \Phi 1.$$

Also in the multi-articulated link knee joint 800 according to the eighth embodiment, an auxiliary driver (not illustrated) is controlled in accordance with the obtained bending angle. Since the first acceleration sensor 860 and the second acceleration sensor 862 as the relative position detector are provided at the knee unit 10, even with auxiliary drivers of different types, the bending angle of the knee unit 10 can be detected.

In the eighth embodiment, the first acceleration sensor 860 and the second acceleration sensor 862 may be used in conjunction with an angular velocity sensor (gyroscope). In this case, more accurate angle detection can be performed.

The present invention has been described above on the basis of the embodiments. The embodiments are merely examples, and thus it should be understood by a person skilled in the art that combinations of components or processing processes of the examples may include various variations and that such variations are also within the scope of the present invention.

In the present specification, the present invention has been described with the example of multi-articulated link knee joint having four axes. However, the present invention is also applicable to a uniaxial knee joint. Specifically, the method of detecting the bending angle of the knee unit described in the first embodiment, the third embodiment, the fourth embodiment, the fifth embodiment, and the eighth embodiment described above is also applicable to a uniaxial knee joint.

What is claimed is:
1. A multi-articulated link knee joint comprising:
a knee unit in which an upper link unit is structured to rotate relative to a lower link unit by a four-articulated link mechanism including four link units consisting of the upper link unit, the lower link unit, and a front link unit and a rear link unit structured to rotatably support the upper link unit relative to the lower link unit;
a relative position detector structured to detect a distance from the upper link unit to the front link unit; and
an angle detector structured to obtain a bending angle of the knee unit from the detected distance,
wherein the relative position detector includes:
a magnet provided at the upper link unit; and
a magnetic sensor provided at the front link unit, the magnetic sensor structured to detect an intensity of a magnetic field generated by the magnet.

* * * * *